United States Patent
Thompson et al.

[11] Patent Number: 5,906,641
[45] Date of Patent: *May 25, 1999

[54] BIFURCATED STENT GRAFT

[75] Inventors: Paul J. Thompson, New Hope, Minn.; George W. Du, Clearwater, Fla.

[73] Assignee: Schneider (USA) Inc, Plymouth, Minn.

[21] Appl. No.: 09/022,256

[22] Filed: Feb. 11, 1998

Related U.S. Application Data

[60] Provisional application No. 60/047,749, May 27, 1997.
[51] Int. Cl.⁶ ............................... A61F 2/06; A61F 2/04
[52] U.S. Cl. ................................. 623/1; 623/12; 606/191
[58] Field of Search .................... 623/1, 11, 12, 623/66; 606/191, 192, 193, 194, 195

[56] References Cited

U.S. PATENT DOCUMENTS

| | | | |
|---|---|---|---|
| 4,553,545 | 11/1985 | Maass et al. | 128/341 |
| 4,655,771 | 4/1987 | Wallsten | 623/1 |
| 4,732,152 | 3/1988 | Wallsten et al. | 128/343 |
| 4,738,740 | 4/1988 | Pinchuk et al. | 156/167 |
| 4,760,849 | 8/1988 | Kropf | 128/341 |
| 4,771,773 | 9/1988 | Kropf | 128/303 |
| 4,848,343 | 7/1989 | Wallsten et al. | 128/343 |
| 4,850,999 | 7/1989 | Planck | 623/1 |
| 4,875,480 | 10/1989 | Imbert | 128/343 |
| 4,954,126 | 9/1990 | Wallsten | 600/36 |
| 4,990,151 | 2/1991 | Wallsten | 606/108 |
| 5,019,090 | 5/1991 | Pinchuk | 606/194 |
| 5,026,377 | 6/1991 | Burton et al. | 606/108 |
| 5,061,275 | 10/1991 | Wallsten et al. | 623/1 |
| 5,071,407 | 12/1991 | Termin et al. | 604/104 |
| 5,084,065 | 1/1992 | Weldon et al. | 623/1 |
| 5,092,877 | 3/1992 | Pinchuk | 623/1 |
| 5,163,951 | 11/1992 | Pinchuk et al. | 623/1 |
| 5,197,976 | 3/1993 | Herweck et al. | 623/1 |
| 5,201,757 | 4/1993 | Heyn et al. | 606/198 |
| 5,356,423 | 10/1994 | Tihon et al. | 606/194 |
| 5,360,443 | 11/1994 | Barone et al. | 623/1 |
| 5,405,380 | 4/1995 | Gianotti et al. | 623/1 |
| 5,415,664 | 5/1995 | Pinchuk | 606/108 |
| 5,464,408 | 11/1995 | Duc | 606/108 |
| 5,484,444 | 1/1996 | Braunschweiler et al. | 606/108 |
| 5,534,287 | 7/1996 | Lukic | 427/2.25 |
| 5,562,724 | 10/1996 | Vorwerk et al. | 623/1 |
| 5,562,725 | 10/1996 | Schmitt et al. | 623/1 |
| 5,575,818 | 11/1996 | Pinchuk | 623/1 |
| 5,591,172 | 1/1997 | Bachmann et al. | 606/108 |
| 5,591,226 | 1/1997 | Tretroola et al. | 623/1 |
| 5,607,466 | 3/1997 | Imbert et al. | 623/1 |
| 5,609,627 | 3/1997 | Goicoechea | 623/1 |
| 5,628,783 | 5/1997 | Quiachon | 623/1 |
| 5,628,787 | 5/1997 | Mayer | 623/1 |
| 5,628,788 | 5/1997 | Pinchuk | 623/1 |
| 5,632,772 | 5/1997 | Alcime et al. | 623/1 |
| 5,639,278 | 6/1997 | Dereume et al. | 623/1 |
| 5,645,559 | 7/1997 | Hachtman et al. | 606/198 |
| 5,653,747 | 8/1997 | Dereume | 623/1 |
| 5,662,703 | 9/1997 | Yurek et al. | 623/1 |
| 5,667,486 | 9/1997 | Mikulich et al. | 604/8 |
| 5,693,087 | 12/1997 | Parodi | 623/1 |

(List continued on next page.)

*Primary Examiner*—David H. Willse
*Assistant Examiner*—Dinh X. Nguyen
*Attorney, Agent, or Firm*—Frederick W. Niebuhr

[57] ABSTRACT

A bifurcated stent graft implantable in branched internal passageways includes an open-frame stent latticework formed of helically wound structural strands, and a graft sleeve formed of interwoven textile strands. The sleeve is substantially impervious to fluids and is adjustable along with the graft between a nominal state and radially-reduced axially-elongated state, according to substantially the same relationship of radial reduction versus axial elongation. The sleeve and stent are bonded to one another at least at proximal and distal end regions of the stent graft. The sleeve preferably is surrounded by the stent, and incorporates a flow dividing feature in the form of an axially extending seam. The seam brings together portions of the sleeve that otherwise would be circumferentially spaced apart in the tubular sleeve shape. The stent latticework and graft sleeve can be coextensive, the sleeve can extend distally beyond the latticework, or the latticework can extend proximally beyond the sleeve, depending on the intended use. In other alternative embodiments, the sleeve can surround the latticework.

34 Claims, 4 Drawing Sheets

U.S. PATENT DOCUMENTS

| | | | |
|---|---|---|---|
| 5,700,269 | 12/1997 | Pinchuk et al. | 606/108 |
| 5,733,325 | 3/1998 | Robinson et al. | 623/1 |
| 5,741,325 | 4/1998 | Chaikof et al. | 623/1 |
| 5,755,770 | 5/1998 | Ravenscroft | 623/1 |
| 5,755,772 | 5/1998 | Evans et al. | 623/1 |
| 5,755,775 | 5/1998 | Trerotola et al. | 623/1 |
| 5,769,882 | 6/1998 | Fogarty | 623/1 |

BIFURCATED STENT GRAFT

This application claims the benefit of priority of Provisional Application No. 60/047,749 entitled "Bifurcated Stent Graft," filed May 27, 1997.

BACKGROUND OF THE INVENTION

The present invention relates to body implantable devices, and more particularly to the prostheses incorporating the characteristics of stents and grafts, and having a flow dividing capability useful for implantation in branched blood vessels.

A variety of treatment and diagnostic procedures involve devices intraluminally implanted into the body of a patient. Among these devices are stents, such as disclosed in U.S. Pat. No. 4,655,771 (Wallsten). The Wallsten devices are tubular, braided structures formed of helically wound thread elements. The stents are deployed using a delivery catheter With the stent positioned at the intended treatment site, an outer tube of the delivery catheter is withdrawn, allowing the stent to radially expand into a substantially conforming surface contact with a blood vessel wall or other tissue.

Thread elements or strands formed of metal are generally favored for applications requiring flexibility and effective resistance to radial compression after implantation. Metal strands can be thermally formed by a moderately high temperature age-hardening process while mounted on a mandrel in the desired configuration. The strands, due to their high modules of elasticity, cooperate to provide the needed strength. Strand flexibility also permits a radial compression and axial elongation of the stent that facilitates intraluminal delivery of the stent to the treatment site. Because the self-expanding stent generally remains at least slightly radially compressed after fixation, its elastic restoring force can provide acute fixation.

The favorable combination of strength and flexibility is due largely to the properties of the strands after they have been age-hardened or otherwise thermally treated. The braid angle of the helical strands and the axial spacing between adjacent strands also influence strength and stability. Age-hardening processes are described in U.S. Pat. No. 5,628,787 (Mayer) and U.S. Pat. No. 5,645,559 (Hachtman, et al.).

An alternative stent construction features plastically deformable metallic structures, which also can be composed of helically wound metallic strands. Such stent does not require an outer tube or other feature to maintain it in a reduced-radius state during delivery. However, radial expansion requires a dilatation balloon or other expansion means.

Regardless of whether stents are self-expanding or plastically deformable, they characteristically have an open mesh or open frame construction, or otherwise are formed with multiple openings to facilitate radial enlargements, and to allow tissue ingrowth. Such stents typically expand axially or longitudinally as they radially contract, and in the case of resilient stents, also axially contract as they radially expand.

Prostheses with more tightly woven strands are known. For example, U.S. Pat. No. 4,681,110 (Wiktor) discloses a flexible tubular liner insertable into the aorta to treat an aneurysm. The liner is a tight weave of flexible plastic strands, designed to elastically expand against the aneurysm to direct blood flow past the aneurysm. The tight weave is intended to minimize leakage, so that the liner can effectively shunt blood through to eliminate the aneurysmal sac from the blood path.

The Wiktor device and others like it notwithstanding, those of skill in the art have continued to encounter difficulty in providing a device that simultaneously accommodates the competing needs of low permeability, strength and flexibility for radial compression and expansion. One known response to this difficulty is a combination stent graft, in which a compliant but substantially fixed-radius and tightly woven graft is sutured or otherwise coupled to a radially expandable stent. Upon release, the stent is intended to radially expand to the graft diameter. This requires a careful matching of the graft diameter with the lumen diameter at the treatment site. Otherwise, either an oversized graft is compressed between the stent and body tissue with undesirable folding or gathering of the graft material, or an undersized graft prevents the stent from radially expanding sufficiently to anchor the device.

Another difficulty arises from the fact that the stent layer and graft layer, even when they are constructed to undergo combined radial contraction and axial elongation, behave according to different relationships governing the amount of radial reduction for a given axial increase. When the stent framework elongates a greater amount for a given radial reduction, elongation of the composite structure tends to tear the bond joining the graft and the stent. Conversely, if the graft layer undergoes greater axial expansion, an unwanted increase in bending stiffness causes localized reductions in diameter when the stent graft is bent around tight radii. Negotiation through tortuous vascular passageways becomes more difficult, and in some instances impossible.

Several prosthesis constructions have been suggested for composite braided structures that combine different types of strands, e.g., multi filament yarns, monofilaments, fusible materials and collagens. Examples are found in International Patent Publications No. WO 91/10766, No. WO 92/16166, No. WO 94/06372, and No. WO 94/06373. A highly favorable combination of strength, resistance, range of treatable lumen diameters and low permeability has been achieved by woven composite devices featuring textile strands interbraided with either cold-worked or thermally set structural strands, as disclosed in U.S. patent applications Ser. No. 08/640,062 and Ser. No. 08/640,091, both filed Apr. 30, 1996 and assigned to the assignee of this application. Although such devices are well suited for a wide range of procedures, there are costs and complexities inherent in interweaving different types of strands.

The application of stent grafts to branched vessels is known, for example as disclosed in U.S. Pat. No. 5,522,880 (Barone, et al.), and U.S. Pat. No. 5,507,769 (Marin, et al.). The foregoing problems apply to stent grafts in general, and thus confront designers of bifurcated stent grafts as well.

Therefore, it is an object of the present invention to provide a bifurcated prosthesis structure that affords the advantages of stents and grafts, yet does not require an interbraiding of structural strands and textile strands.

Another object is to provide a process for manufacturing a bifurcated stent graft in a manner that better ensures that the open-frame structural layer and the low-permeability fabric layer remain securely fixed to one another as they undergo radial and axial enlargements and reductions.

A further object is to provide a bifurcated prosthesis that incorporates highly permeable open areas and low permeability covered areas, and thus is adapted for selective axial positioning to shunt blood flow where required while remaining open to branches of the vessel under treatment.

Yet another object is to provide a system, incorporating a bifurcated stent graft, that is less costly to manufacture and easier to implant.

SUMMARY OF THE INVENTION

To achieve these and other objects, there is provided an implantable prosthesis for branched internal passageways.

The prosthesis includes a tubular open-frame structural member adjustable between a nominal state and a radially-reduced axially-elongated state according to a first relationship of radial reduction vs. axial elongation. The prosthesis further includes a compliant fluid flow guide formed of textile strands, also adjustable between a nominal state and a radially-reduced axially-elongated state, according to a second relationship of radial reduction vs. axial elongation substantially equivalent to the first relationship. The fluid flow guide includes an axially-extending first region along which the fluid flow guide is tubular to provide a primary fluid flow conduit.

The structural member and the fluid flow guide are joined to one another to undergo radial enlargements and contractions in concert. A selected one of the structural member and the fluid flow guide surrounds the other. A flow dividing feature, provided along a second axially-extending region of the fluid flow guide, provides a plurality of secondary fluid flow conduits along the second region. Each of the secondary conduits is open to the primary conduit.

In one particularly preferred construction, the structural member is a stent formed of interconnected structural strands in first and second sets of helices. The helices are wound in opposite directions to form a first braid angle with respect to a longitudinal axis of the stent when the stent is in the nominal state. Further in this arrangement, the flow guide is a sleeve or graft formed of textile strands. The textile strands are wound in third and fourth sets of helices, oppositely directed to form a second braid angle with respect to the longitudinal axis when the sleeve is in its nominal state. The first and second braid angles are within five degrees of one another, more preferably within about three degrees, and most preferably within about one degree. In a helical weave, the braid angle is an important factor in determining the degree of radial reduction for a given amount of axial elongation. Thus, the matching of braid angles, augmented by appropriately matching the stent and sleeve as to size when each is in the nominal state, ensures that the stent and sleeve behave according to substantially the same relationship of radial reduction vs. axial elongation. Accordingly, there is no tendency in the stent to tear free of the sleeve due to a more rapid axial elongation for a given radial reduction. Conversely, there is no unwanted increase in bending stiffness due to an axial elongation of the sleeve that exceeds that of the stent.

A variety of structural modifications and versions of the prosthesis can be practiced according to the invention. The stent may extend only to the proximal end of the graft, or may extend proximally beyond the graft. Further, the stent may extend only along the first region of the sleeve, or alternatively extend distally to encompass the second region of the sleeve as well.

According to one aspect of the invention, a body insertable prosthesis includes a compliant and substantially fluid impervious sleeve with tubular proximal and distal end regions. A tubular open-frame structural member surrounds the sleeve and is fixed to the sleeve at least along the tubular end regions, whereby the structural member and the sleeve are adjustable in concert between a nominal state and a reduced-radius state. A flow dividing feature defines a plurality of medial fluid flow conduits along a medial region of the sleeve for accommodating fluid flow axially through the sleeve. Each of the medial conduits is open to the proximal and distal end regions of the sleeve.

Preferably the sleeve is formed of a continuous fabric wall, and the flow dividing feature comprises a coupling of two portions of the fabric wall circumferentially spaced apart from one another when the sleeve as in a cylindrical shape. The coupling can involve the sleeve alone, leaving the structural member in its tubular configuration. This results in a more stable stent graft structure. Because the stent remains cylindrical, its response to external forces remains more consistent over its entire axial length. The device is easier to fabricate, since only the sleeve needs to be formed into a non-cylindrical shape.

The arrangement also enhances implantation. Having the stent surround the sleeve, rather than vice versa, improves acute and chronic fixation. Moreover, a system including the prosthesis and a pair of distal cylindrical stent grafts is easier to implant. This is because the open distal end of the prosthesis functions like a funnel to guide the insertion of the cylindrical stent grafts, each to an associated one of the medial fluid flow conduits.

The preferred flow dividing feature is stitching in the form of one or more seams through portions of the graft or sleeve that would be circumferentially spaced apart from each other if the sleeve remained in the tubular shape. A single, axially extending stitching line forms two fluid flow conduits from the tubular sleeve. Typically, the circumferential spacing between the sleeve portions is about 180 degrees, in which case the two fluid flow conduits are substantially the same size. A pair of spaced apart seams can be used to form three side-by-side fluid flow conduits. Alternatively, two relatively close stitching lines can be used to form two fluid flow conduits. The sleeve material between the stitching lines can be severed to provide separate tubular legs defining the separate conduits.

Further according to the invention, there is provided a process for making a stamped graft implantable in branched internal passageways, according to the following steps:

(a) providing a tubular stent comprised of a plurality of structural strands and adjustable between a nominal state and a radially-reduced axially-elongated state according to a first relationship of radial reduction vs. axial elongation;

(b) providing a tubular sleeve comprised of a plurality of compliant textile strands, having a nominal state in which the sleeve is substantially the same size and shape as the stent in its nominal state, and adjustable between the nominal state and a radially-reduced axially-elongated state according to a second relationship of radial reduction vs. axial elongation substantially equivalent to the first relationship;

(c) forming a coupling of two otherwise circumferentially spaced apart portions of the sleeve along an axially extending selected region of the sleeve to form at least two side-by-side fluid conduits along the selected region, thus forming the sleeve into a fluid flow guide having a primary fluid conduit along a proximal end region of the sleeve in fluid communication with the side-by-side fluid conduits;

(d) positioning a selected one of the stent and the sleeve within the other of the stent and sleeve, so that said other surrounds the selected one, and with the selected one so positioned, bringing the stent and sleeve into an engagement; and (e) while maintaining the engagement, binding the stent and the sleeve together to form a composite stent graft.

Thus, in accordance with the present invention, a bifurcated prosthesis affords the advantages of stents and grafts without requiring an interbraiding of structural strands and textile strands. The prosthesis is formed with an open-frame structural layer and a fluid impervious graft fabric layer. Although formed separately, the structural and fabric layers are integrally fixed to one another. Further, because these layers behave according to the same relationship governing axial expansion vs. radial reduction, radial expansions and contractions do not unduly strain the bond or compromise its integrity. The prosthesis is easier and less costly to fabricate, especially when the structural layer surrounds the graft fabric layer. This configuration permits the structural layer to remain in a tubular configuration along its entire axial length, while only the interior graft layer is specially shaped to provide the number of fluid flow conduits desired.

IN THE DRAWINGS

For a further appreciation of the above and other features and advantages, reference is made to the following detailed description and to the drawings, in which.

DETAILED DESCRIPTION OF THE PREFERRED EMBODIMENTS

Figure 1:
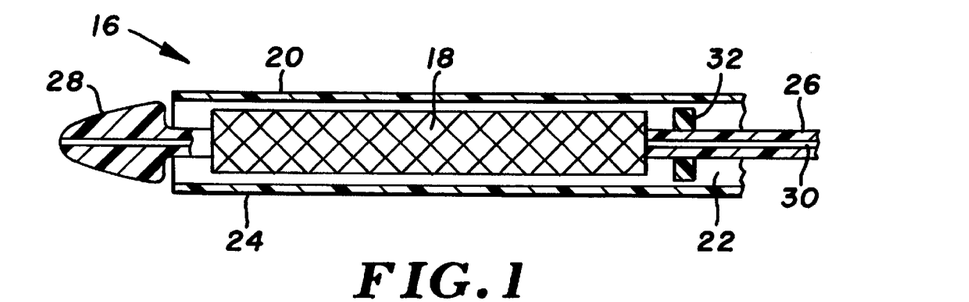
FIG. 1 is a side elevation, partially in section, showing a bifurcated stent graft constructed in accordance with the present invention contained within the deployment device.

Turning now to the drawings, there is shown in FIG. 1 a deployment device 16 for delivering a bifurcated stent graft 18 to an intended fixation site or treatment site within a body lumen, then controllably releasing the stent graft for radial self-expansion and fixation within the body lumen.

The device includes an elongate and flexible outer catheter 20 constructed of a bio-compatible polymer such as polyurethane. A central lumen 22 runs the length of catheter 20. A distal end region 24 of the outer catheter surrounds stent graft 18. An inner catheter 26 is contained within lumen 22 and runs along the entire length of the outer catheter. At the distal end of inner catheter 26 is a tapered distal tip 28 which extends beyond the outer catheter. Stent graft 18 surrounds inner catheter 26, confined between the inner and outer catheters. A lumen 30 in the inner catheter accommodates a flexible guide wire tracked by device 16 as it is advanced toward the treatment site.

Bifurcated stent graft 18 is formed of resilient materials, and in FIG. 1 is shown elastically compressed into a radially-reduced and axially-elongated delivery state. Outer catheter 20 maintains the stent graft in the delivery state against its elastic restoring force. An annular detent 32, mounted to inner catheter 26, occupies a space between the inner and outer catheters to limit proximal travel of the stent graft relative to the inner catheter. As outer catheter 20 is moved proximally relative to inner catheter 26, the detent prevents stent graft 18 from following the outer catheter.

Catheters 20 and 26, while maintaining stent graft 18 in the delivery state, are moved translumenally to deliver the stent graft to the site. Once the stent graft is positioned as intended, inner catheter 26 is held stationary while outer catheter 20 is withdrawn proximally. The inner catheter, because of detent 32, maintains the stent graft properly aligned as the stent graft radially self-expands toward an intimate contact with tissue at the treatment site. The stent graft does not expand completely to the relaxed state (i.e., its condition when not subject to any external force). Consequently, the stent graft exerts a residual force on surrounding tissue that tends to acutely fix the prosthesis. At this point, the stent graft has a diameter larger than the diameter of distal tip 28, so that the inner catheter and tip can be proximally withdrawn to leave the stent graft in place.

Figure 2:
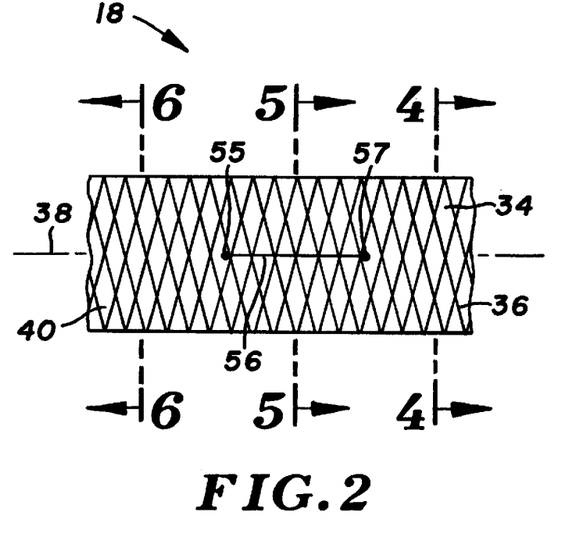
FIG. 2 shows the stent graft in side elevation in an unconstrained, radially expanded state.
Figure 3:
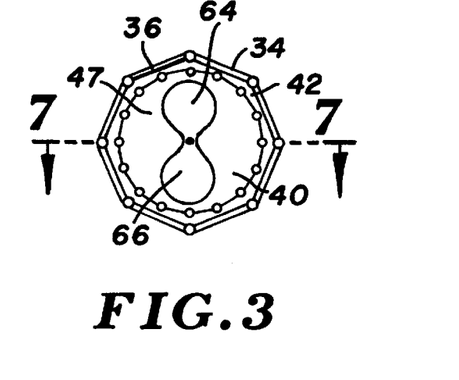
FIG. 3 is an end elevation of the radially expanded stent graft.

In FIGS. 2 and 3, bifurcated stent graft 18 is shown in its nominal or relaxed state, indicating the lack of an external force. The stent graft is formed of several concentric layers which act in concert during radial expansions and contractions. The radially outside layer is a stent 34, which is a framework or latticework of resilient monofilament structural strands 36. Strands 36 are arranged in two sets of parallel helices wound in opposite directions about a common longitudinal axis 38. The strands intersect one another to define rhombotic interstices and a braid angle alpha ($\alpha$) bisected by the longitudinal axis. The braid angle is in the range of about 60–150 degrees, more preferably about 90–140 degrees.

The braid angle is defined with reference to the nominal state of stent 34. Compression of the stent graft into the delivery state substantially reduces the braid angle. At the same time, the braid angle influences the relationship between radial compression and axial elongation of the stent graft. Smaller braid angles result in less axial shortening for a given amount of radial enlargement. Conversely, with a larger braid angle, the same radial expansion results in more axial shortening. For a given strand size and strength, a larger braid angle imparts greater resistance to radial compression and more positive acute fixation.

Structural strands 36 are elastic, strong, bio-compatible, hemo-compatible, and resistant to corrosion and fatigue. Suitable materials include certain stainless spring steels, cobalt-based alloys, titanium alloys, and clad composites disclosed in U.S. Pat. No. 5,628,787. Several preferred cobalt-based alloys are sold under the brand names Elgiloy, Phynox, and MP35N. Strands 36 also can be formed of polymers, including PET, polypropylene, PEEK, high density polyethylene, polysulfone, acetyl, PTFE, FEP, and polyurethane. Suitable strand diameters range from about 0.002 inches to about 0.015 inches.

The latticework surrounds a graft 40 which is a textile sleeve or fabric sheeting formed of multiple textile strands interwoven with one another. The textile strands are braided in oppositely directed helices and intersect one another to define the braid angle theta (θ) substantially the same as braid angle alpha of the latticework. More particularly, the two braid angles should be within about five degrees of one another, more preferably are within three degrees, and most preferably are within about one degree.

The textile strands preferably are multiple-filament yarns, although they can be monofilaments. Either way, the textile strands are much finer than the structural strands, ranging from about 10–400 denier. The multiple-filament yarns generally have a high degree of compliance, and also preferably are substantially inextensible. Preferred yarns are composed of PET (Dacron). Other acceptable materials include polypropylene, a high molecular weight polyethylene sold under the brand name Spectra, polyurethane, high density polyethylene, polyethylene, silicone, PTFE, polyolefins, and ePTFE.

Because of the fineness of the textile strands and a close or tight weave, sleeve 40 can be microporous yet essentially impervious to body fluids. The textile sheeting of the graft is highly compliant, tending to conform to the changes in shape of stent 34 as the stent graft either radially self-expands or is radially reduced. The shape of the stent essentially determines the shape of the stent graft.

Despite the compliant nature of the graft, proper matching of the graft and stent is critical to achieving high performance. In general terms, the stent latticework and graft sleeve are matched so that when adjusted between their nominal states and their delivery states, they behave according to about the same relationship of radial reduction vs. axial elongation. The appropriate matching in this embodiment involves forming the latticework and the sleeve with about the same braid angle, i.e., θ=α. In other embodiments, appropriate matching may require at least a slight difference in angles θ and α, as discussed below.

Stent 34 and graft 40 are integrally secured to one another by an adhesive layer 42, preferably silicone. The silicone adhesive forms an extremely thin (e.g., 0.005 inches or 0.12 mm) layer between the stent and graft, adhering to both. Due to the matching of the latticework and sleeve braid angles, adhesive layer 42 is required to accommodate only slight movement of the sleeve relative to the latticework during radial expansions and contractions of the stent graft. Matching avoids a difference in axial elongation rates that otherwise would unduly stress the adhesive layer and/or cause unwanted stiffness in resistance to bending. As a result, the stent graft is usable over a wider range of radii, elastically compressible to a smaller radius, and better able to negotiate tortuous or serpentine arterial passages.

Figure 4:
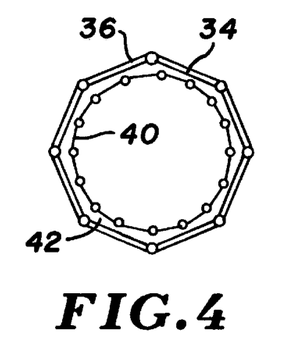
FIG. 4 is a sectional view taken along the line 4—4 in FIG. 2.
Figure 5:
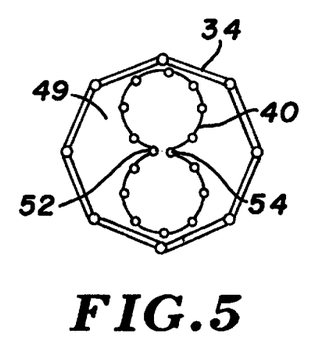
FIG. 5 is a sectional view taken along the line 5—5 in FIG. 2.
Figure 6:
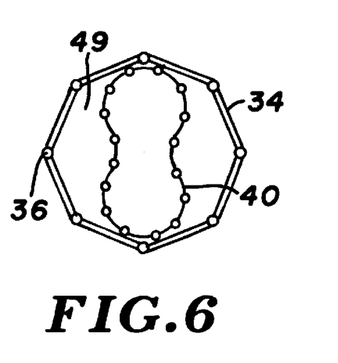
FIG. 6 is a sectional view taken along the line 6—6 in FIG. 2.
Figure 7:
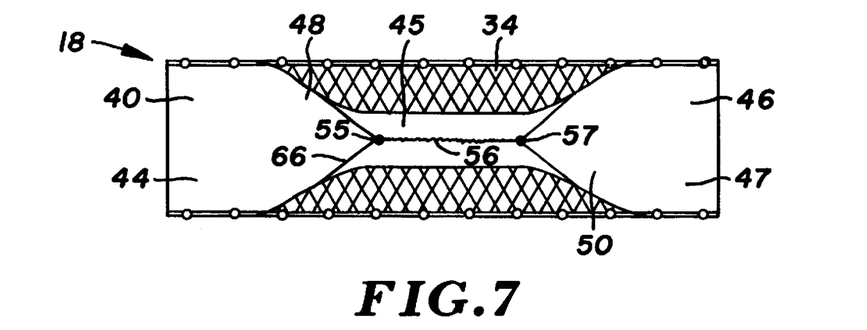
FIG. 7 is a sectional view taken along the line 7—7 in FIG. 3.

Stent 34 is shaped as a tube, more particularly a circular cylinder. Graft 40, along a proximal end region 44 and a distal end region 46, likewise is circular cylindrical in shape. Along an axially extending medial region 45, the graft transverse section resembles a figure eight rather than a circle as seen in FIGS. 4 and 5. Finally, the graft includes proximal and distal transition regions 48 and 50 between the medial region and the end region, where the transverse section changes gradually from one shape to the other. FIG. 6 is a section taken along transition region 48, illustrating one of the intermediate transverse sections. Transition regions 48 and 50 are shown in FIGS. 3 and 7 where an inside surface 47 of the graft is visible, and also are shown in FIG. 5 where an outside surface 49 of the graft is visible. As perhaps best seen in FIGS. 5–7, stent 34 is not shaped to conform to the graft, but rather remains tubular.

The figure eight profile along medial region 45 is caused by an axially extending coupling of two opposed portions 52 and 54 of the graft. In the absence of the coupling, the sleeve would be cylindrical along its full length, and portions 52 and 54 would be circumferentially spaced apart from one another by about 180 degrees. As seen in FIGS. 2 and 7, the coupling is a straight line seam 56 extending in the axial direction. The seam is sewn in zigzag stitching, preferably with a stretchable stitch. If desired, radiopaque markers 55 and 57 can be provided at opposite ends of the seam. Seam 56 overcomes the tendency of sleeve 40 to assume the tubular form, and thus shapes the graft to provide the medial and transition regions.

Figure 8:
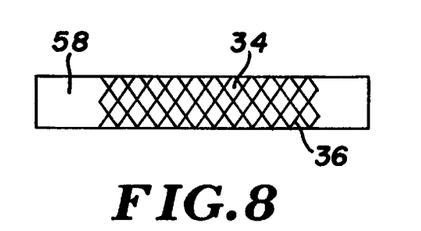
FIGS. 8–12 schematically illustrate the fabrication of the bifurcated stent graft.

Fabrication of the bifurcated stent graft initially involves separate formation of stent 34 and graft 40. Formation of the stent includes winding structural strands 36 in helices of the desired size and axial spacing, from multiple bobbins onto a cylindrical mandrel 58 (FIG. 8). For further details of this winding process and other manufacturing stages with references to a cylindrical non-bifurcated device, reference is made to U.S. patent application Ser. No. 08/946,906 entitled "Stent Graft with Braided Polymeric Sleeve," filed Oct. 8, 1997, and assigned to the assignee of this application.

After their removal from the mandrel, structure strands 36 are heat treated to determine the shape of the latticework in its nominal state. Metallic monofilament strands are age hardened within a furnace in a near vacuum or other protective atmosphere. Alternatively, the structural strands can be formed of a recovery metal, in which case the latticework is plastically deformable when maintained below an activation temperature. In this context, the nominal shape is the shape to which the latticework returns when heated at least to the activation temperature. A titanium nickel alloy known as "Nitinol" is suitable for this type of strand. As a further alternative, the latticework can be formed of plastically deformable strands other than recovery metal strands. In yet another alternative, thermoplastic structural strands are thermally set about a mandrel, at much lower temperatures than their metallic counterparts.

Figure 9:
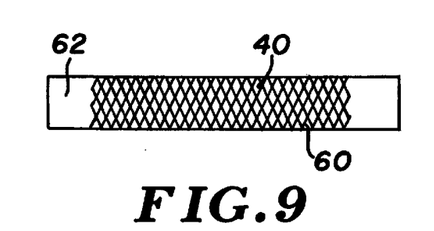
Figure 10:
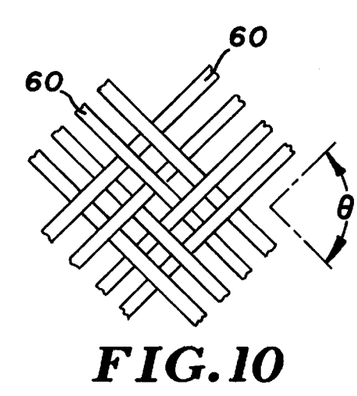

Graft sleeve 40 is formed by braiding textile strands 60 about a shaping mandrel 62 (FIGS. 9–10), again in two sets of parallel, oppositely directed helices. The multi-filament yarns are wound at a braid angle theta chosen with respect to braid angle alpha of the latticework, to closely match the geometrical diameter and elongation properties of the latticework and sleeve when these components are formed into the stent graft. FIG. 10 shows in detail multi-filament yarns 60 interwoven in a two-over-two pattern, and also shows braid angle theta. While wound about mandrel 62, the textile strands are thermally set to give the sleeve its nominal state. Thus, prior to their joinder the latticework and sleeve are formed independently of one another. Further details about forming the sleeve are found in the aforementioned patent application Ser. No. 08/946,906.

Figure 11:
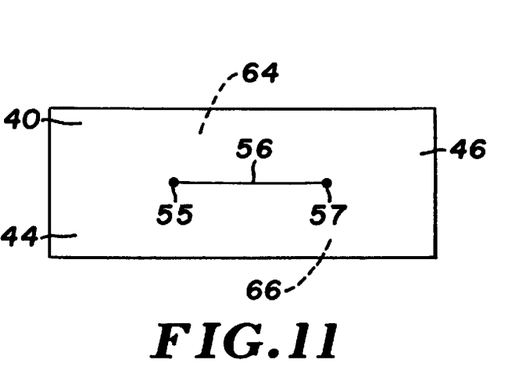

Before assembly of the latticework and sleeve, the sleeve is sewn along medial region 45 to create a flow dividing feature that separates flow of fluids into two separate channels of approximately equal dimension. Seam 56, as noted above, extends axially and draws together opposed sleeve portions 52 and 54 that otherwise would be circumferentially spaced apart about 180 degrees. Thus, seam 56 shapes the graft sleeve, from its original tubular form to a form suitable for use of the sleeve as a fluid flow guide. Along medial region 45, the sleeve forms two fluid flow conduits 64 and 66 of nearly equal size. Along proximal region 44 and along distal region 46, the sleeve continues to define a single fluid flow conduit.

Following their independent formation, the sleeve and latticework are bonded to one another. Preferably, where possible the bond extends circumferentially about the interface between the latticework interior surface and the sleeve exterior surface. The bond should be highly uniform, to avoid stress concentrations and insure more uniform behavior of the stent graft during bending, radial expansions and radial contractions. To this end, a siloxane polymer (silicone) adhesive is applied as a uniformly thick coating to latticework 34, although it can be applied to the sleeve or to both the latticework and sleeve. To enhance uniformity, the silicone is dispersed in an organic solvent of xylene and THF (tetrahydrafuran) at a concentration of about 6% in the silicone polymer, by weight. Suitable alternative organic solvents include toluene and trichloroethylene. Suitable alternative polymers include flurosilicone and polycarbonate urethane. Alternative adhesives include polycarbonate urethanes such as disclosed in U.S. Pat. No. 5,229,431 (Pinchuk).

The polymer/solvent solution is sprayed onto the latticework to a uniform thickness of about 0.005 inches over the entire latticework surface. Alternative approaches employ a polymeric adhesive in powdered form, or apply the polymer in liquid form by a hot melt process. For further details, see the aforementioned Ser. No. 08/946,906 application.

Figure 12:
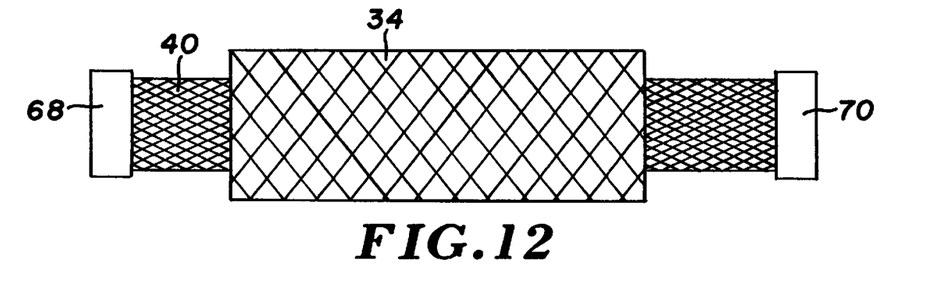

Next, the latticework and sleeve are assembled by axially elongating the sleeve with clamps 68 and 70 to reduce its radius, then inserting the reduced-radius sleeve into latticework 34 while maintaining the latticework in its nominal state. Once inserted, sleeve 40 is allowed to axially shorten and radially expand into a surface engagement with the radially inside surface of the latticework. The thickness of the silicone coating is taken into account in sizing the sleeve and latticework with respect to one another. It has been found advantageous to select the respective radii of sleeve 40 and latticework 34 so that when allowed to expand, the sleeve exerts a slight radially outward force onto the surrounding latticework, with the latticework exerting a counteracting radially inward force upon the sleeve. The counterbalancing forces improve the bond.

At this stage the stent graft is maintained in an oven to cure the silicone polymer adhesive. After curing, the stent graft is removed from the oven and allowed to cool to ambient temperature. The cured silicone polymer adheres to the sleeve and to the latticework, causing stent graft 18, in spite of its three distinct layers, 34, 40 and 42, to behave as a unitary structure.

Figure 13:
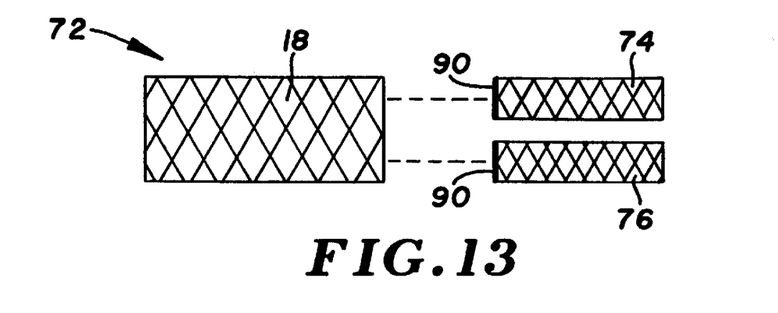
FIG. 13 illustrates a system of implantable prosthetic components including the bifurcated stent graft.

Thus formed, bifurcated stent graft 18 combines favorable attributes of self-expanding stents and of grafts. Latticework 34 provides radial compressibility, self-expansion over a wide range of radii and a residual force sufficient for acute fixation. Sleeve 40 provides reduced permeability so that the bifurcated stent graft is essentially impervious to blood and other body fluids. Consequently, the stent graft is particularly well suited for use in a system 72 for treating an aortic annurism. The system, as seen in FIG. 13. includes stent graft 18 and two cylindrical stent grafts 74 and 76. Each of cylindrical stent grafts 74 and 76 includes a tubular latticework or open frame, and a tubular fabric sleeve, bonded together as described above for bifurcated stent graft 18, except that both the sleeve and latticework remain circular cylindrical in shape. Each of cylindrical stent grafts 74 and 76 is insertable into distal end region 46 of sleeve 40, then further into an associated one of medial fluid conduits 64 and 66 while in a radially reduced state. When allowed to radially self expand, each of the cylindrical stent grafts engages the sleeve along its associated medial conduit, thus anchoring the graft within the associated conduit.

Figure 14:
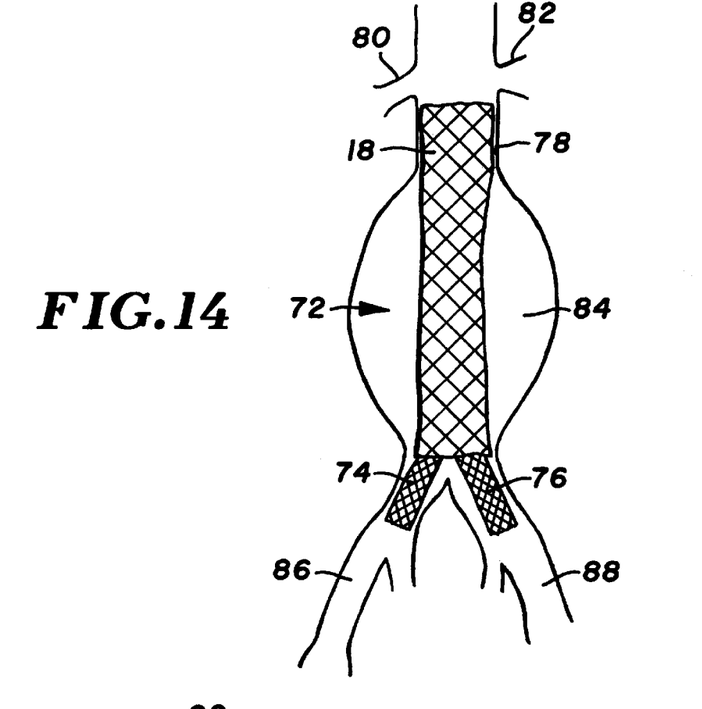
FIG. 14 illustrates the system of FIG. 13 implanted.

FIG. 14 illustrates stent graft system 72 implanted within the aorta 78. Stent graft 18 extends from below renal arteries 80 and 82, to a point above the natural bifurcation, thus to bypass an aneurysm 84. Cylindrical stent grafts 74 and 76 extend distally from the distal end of stent graft 18, each into a corresponding one of iliac arteries 86 and 88. To complete the bypass, each of cylindrical stent grafts 74 and 76 is in fluid communication with one of medial conduits 64 and 66.

To achieve the implantation illustrated in FIG. 14, bifurcated stent graft 18, while maintained in the reduced-radius axially-elongated state in deployment of device 16, is advanced intravascularly, reaching the aorta 78 either through one of iliac arteries 86 and 88, or from above the aorta. When positioned as desired, stent graft 18 is released by withdrawing outer catheter 20 and allowed to self-expand, after which device 16 is withdrawn.

Next, cylindrical stent graft 74, radially reduced within a device similar to device 16 is advanced translumenally to iliac artery 86 and upwardly toward the distal end region 46 of bifurcated stent graft 18. A single conduit along the distal end of the bifurcated graft provides a large capture area that facilitates insertion of cylindrical graft 74. As stent graft 74 is advanced further toward medial region 45, the sleeve along transition region 48 functions as a funnel to guide the proximal end of stent graft 74 toward its associated medial conduit, until the stent graft is inserted within the associated medial conduit. Radiopaque marker 57 at seam 56, and a radiopaque marker 90 at the proximal end of stent graft 74, can be used to confirm entry into the medial conduit. When stent graft 74 has been inserted to the extent desired, it is released from its device and allowed to self-expand into an engagement with sleeve 40 that secures the stent graft. At this point, the device used to deploy the stent graft can be withdrawn.

In substantially the same manner, cylindrical stent graft 76 is advanced along iliac artery 88, and into its associated medial conduit via distal end region 46 of stent graft 18. Once again, the distal end region facilitates initial capture, and transition region 48 acts as a funnel to properly guide the cylindrical stent graft to its associated medial conduit. Release of stent graft 76 allows radial expansion into the securing engagement.

To more effectively address a variety of treatment situations, a variety of alternative embodiment stent grafts can be formed according to the above-discussed process.

Figure 15:
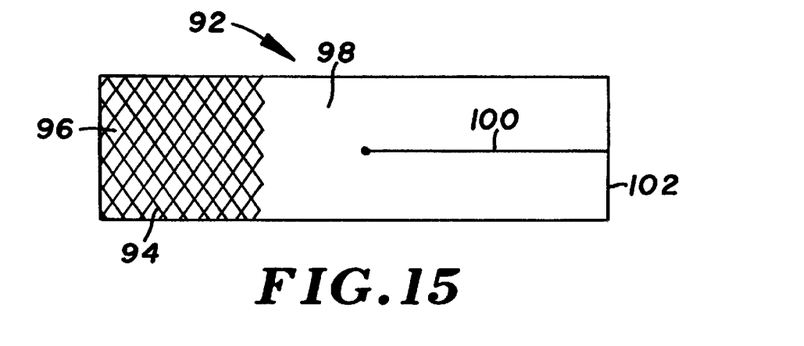
FIG. 15 illustrates an alternative embodiment bifurcated stent graft constructed according to the invention.

FIG. 15 illustrates a stent graft 92 in which a latticework 94 extends axially only along a proximal region 96 of a fabric sleeve 98. In this embodiment, a stitching line 100 extends to a distal end 102 of the sleeve, so that sleeve 98 has two fluid flow conduits at and near the distal end. Forming sleeve 98 of a substantially inextensible multifilament yarn is particularly advantageous in connection with this embodiment, and in other embodiments in which a substantial portion of the sleeve extends unsupported by a latticework.

Figure 16:
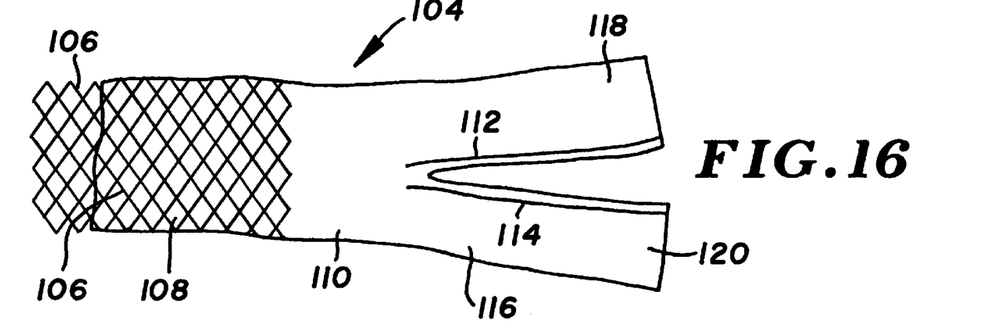
FIG. 16 illustrates another alternative bifurcated stent graft embodiment.

FIG. 16 illustrates another alternative embodiment stent graft 104 in which a latticework 106 extends only along a proximal region 108 of a sleeve 110. Stent graft 104 differs from stent graft 92 in FIG. 15 in several respects. First, latticework 106 extends proximally beyond sleeve 110. This permits use of the latticework to fixate the device with the proximal open portion of the latticework aligned with the renal arteries, to achieve fixation without impeding blood flow. Another difference is that two substantially parallel seams 112 and 114 are formed along a distal region 116 of the sleeve. As in previous embodiments, two fluid flow conduits are formed. Further, however, material between the seams is severed, to form two legs 118 and 120 movable independently of one another. The legs are thus positionable in iliac arteries 86 and 88, either to accept additional cylindrical stent grafts such as 74 and 76, or to complete a bypass without the need for further stent grafts.

Figure 17:
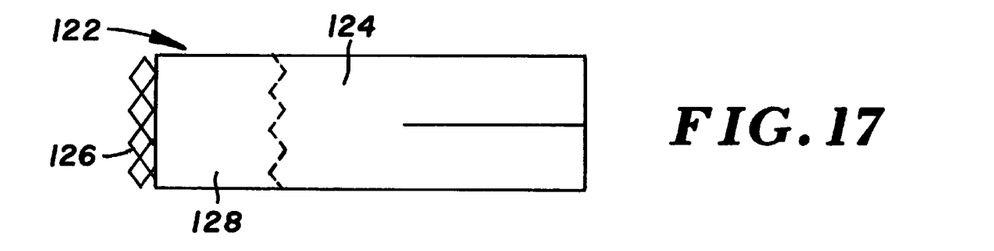
FIG. 17 illustrates a further alternative bifurcated stent graft embodiment.

FIG. 17 illustrates a further alternative embodiment stent graft 122 in which a fabric sleeve 124 surrounds a stent latticework 126. The latticework is provided only along a proximal region 128 of the sleeve. In embodiments of this type, where the graft or sleeve is disposed about the stent or other structural support, the braid angle of the textile strands preferably is between the 100.91 percent and 105.45 percent of the braid angle of the structural strands. In the preceding embodiments, where the graft is disposed inside of the structural support, the braid angle of the textile strands preferably is between 97.72 percent and 102.27 percent of the braid angle formed by the structural strands.

If desired, a modified form of stent graft 122 can be provided, in which the latticework extends for the entire axial length of the sleeve. This enhances structural support, but also requires a shaping of the latticework to bring otherwise circumferentially spaced apart portions of the latticework and sleeve together for dividing the flow within the bifurcated graft. As noted above, when the latticework or stent surrounds the sleeve, only the sleeve need be shaped in this fashion.

Figure 18:
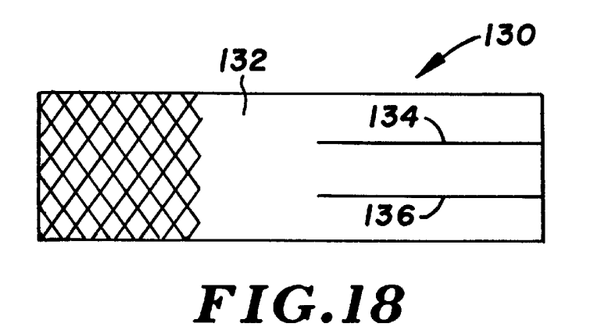
FIGS. 18 and 19 illustrate yet another embodiment bifurcated stent graft.
Figure 19:
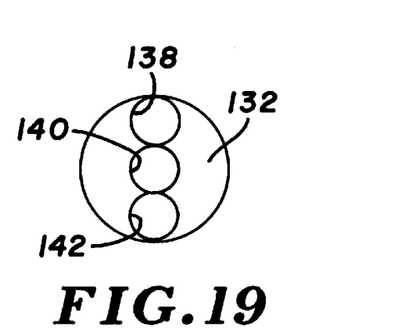

FIGS. 18 and 19 illustrate another embodiment stent graft 130 in which a sleeve 132 is coupled along two seams 134 and 136, spaced apart sufficiently to form three fluid flow conduits 138, 140 and 142 in fluid communication with a single proximal conduit.

Figure 20:
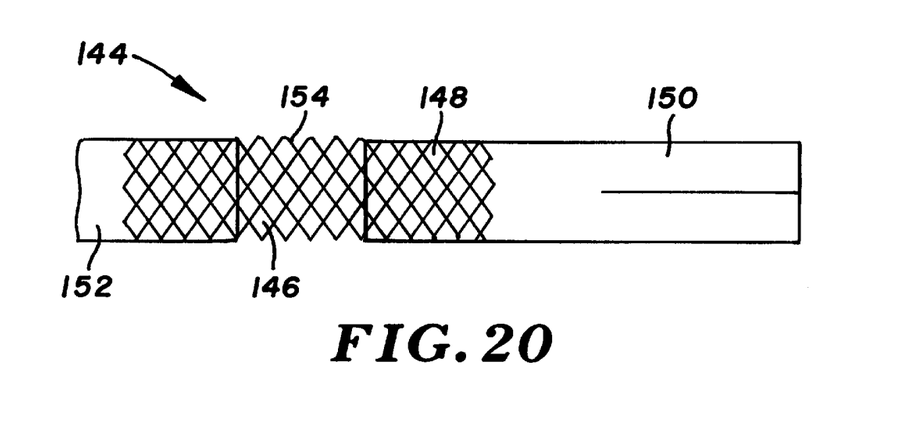
FIG. 20 illustrates a further embodiment stent graft.

FIG. 20 shows another embodiment stent graft 144 in which a stent or latticework 146 extends along a proximal portion 148 of a fabric sleeve 150. Part of the latticework also extends proximally beyond sleeve 150, to surround a tubular sleeve 152 spaced apart from sleeve 150. Each of sleeves 150 and 152 is positionable along an intraluminal location where shunting of the blood flow is desired. An exposed intermediate region 154 between the sleeves is positionable in alignment with a branch of the vessel being treated, so that sent graft 130 can provide the necessary shunting without blocking flow between the main vessel and a branch between the two sleeves.

With all of the aforementioned embodiments, the graft or sleeve can be woven with essentially untwisted (or slightly twisted) multifilament yarns in which the filaments have surface twisting angles of at most about 15 degrees. Such yarns can be formed with noncircular cross sections. More particularly, a desired aspect ratio (w/t or width divided by thickness) is at least two. For more information about these yarns, reference is made to the aforementioned U.S. patent application Ser. No. 08/946,906.

Thus in accordance with the present invention, a bifurcated prosthesis can be fabricated without interbraiding structural strands and textile strands, yet afford the advantages of stents and grafts. The prosthesis incorporates a highly permeable open-frame structural member for support, with a low permeability graft or fabric sleeve either along the entire length of the structural member or selectively leaving an open-framed area exposed, to allow flow from a branch to the artery being treated while the required shunting is accomplished. The stent graft is manufactured in a manner that better ensures that the open-frame structural layer and the low-permeability fabric layer remain securely fixed to one another as they undergo radial and axial enlargements and reductions. Finally, the construction in which the structural member surrounds the fabric layer is particularly effective in facilitating implantation of a system including the bifurcated stent graft and two or more cylindrical stent grafts insertable into the bifurcated prosthesis.

Each of the references cited in the foregoing specification is incorporated in its entirety, and for all purposes.

What is claimed is:

1. An implantable prosthesis for branched internal passageways, including:

an open-frame structural member adjustable between a nominal state and a radially-reduced axially-elongated state according to a first relationship of radial reduction vs. axial elongation;

a fluid flow guide formed of textile strands, substantially impervious to fluids and adjustable between a nominal state and a radially-reduced axially-elongated state according to a second relationship of radial reduction vs. axial elongation substantially equivalent to said first relationship, said fluid flow guide including an axially-extending first region along which the fluid flow guide is tubular to provide a primary conduit;

wherein the structural member and the fluid flow guide are joined to one another to undergo radial enlargements and contractions in concert, with a selected one of the structural member and fluid flow guide surrounding the other; and a flow dividing feature along a second axially-extending region of the fluid flow guide, to provide along the second region at least two secondary conduits, each secondary conduit open to the primary conduit.

2. The prosthesis of claim 1 wherein:

the textile strands forming the fluid flow guide are substantially inextensable.

3. The prosthesis of claim 1 wherein:

the structural member is tubular at least along a portion thereof adjacent the first region, and said first region and said portion of the structural member have substantially the same radii when in their respective nominal states.

4. The prosthesis of claim 1 wherein:

the structural member extends axially at least over the complete length of the fluid flow guide.

5. The prosthesis of claim 1 wherein:

a portion of the structural member extends proximally beyond a proximal end of the fluid flow guide.

6. The prosthesis of claim 1 wherein:

a distal portion of the fluid flow guide extends distally of the structural member.

7. The prosthesis of claim 1 wherein:

the second region comprises a medial region of the fluid flow guide disposed between proximal and distal end regions of the guide, and said first region comprises the proximal and distal end regions.

8. The prosthesis of claim 1 wherein:

the fluid flow guide is formed of a continuous fabric wall that tends to assume a cylindrical shape when not subject to an external force, and the flow dividing feature comprises a coupling of selected portions of the fabric wall that are circumferentially spaced apart from one another when the fluid flow guide is in the cylindrical shape.

9. The prosthesis of claim 8 wherein:

the coupling extends axially along the fluid flow guide.

10. The prosthesis of claim 8 wherein:

said selected portions of the fabric wall are spaced apart about 180 degrees when the fluid flow guide is in the cylindrical shape, and the fluid flow guide when shaped by said coupling forms two secondary conduits about equal to one another in size.

11. The prosthesis of claim 8 wherein:
the structural member surrounds the fluid flow guide, and the at least one coupling comprises a line of stitching through said portions of the fabric wall.

12. The prosthesis of claim 11 wherein:
the coupling includes two adjacent stitchings through the fabric wall, with fabric portions between the adjacent stitchings severed to form separate legs along the second region of the fluid flow guide.

13. The prosthesis of claim 1 wherein:
the fluid flow guide surrounds the structural member.

14. The prosthesis of claim 1 wherein:
the structural member is formed of structural strands wound in first and second sets of helices in opposite directions to form a first braid angle;
the textile strands are arranged in third and fourth sets of helices wound in opposite directions to form a second braid angle; and
the first and second braid angles are within about five degrees of one another.

15. The prosthesis of claim 14 wherein:
the first and second braid angles are within about three degrees of one another.

16. An implantable system of prosthetic components, including the prosthesis of claim 1, and further including:
a plurality of tubular stent grafts, each tubular stent graft being adjustable between a nominal state and a radially-reduced axially-elongated state, each tubular stent graft further being insertable into a corresponding one of the secondary conduits when in its radially-reduced axially-elongated state and, when so inserted, radially expandable into engagement with the fluid flow guide to secure the tubular stent graft within its associated secondary conduit.

17. A process for making a stent graft implantable in branched internal passageways, including:
providing a tubular stent comprised of a plurality of structural strands adjustable between a nominal state and a radially-reduced axially-elongated state according to a first relationship of radial reduction vs. axial elongation;
providing a compliant tubular sleeve comprised of a plurality of textile strands, having a nominal state in which the sleeve is substantially the same size and shape as the stent in its nominal state, and adjustable between the nominal state and a radially-reduced axially-elongated state according to a second relationship of radial reduction vs. axial elongation substantially equivalent to said first relationship;
forming, along an axially-extending selected region of the sleeve, a coupling of selected portions of the sleeve that are circumferentially spaced apart when the sleeve is in the tubular shape, to form at least two side-by-side fluid conduits along the selected region, thus forming the sleeve into a fluid flow guide having a primary fluid conduit along a proximal end region of the sleeve in fluid communication with the side-by-side fluid conduits;
positioning a selected one of the stent and the sleeve within the other of the stent and sleeve, so that said other surrounds the selected one, and with the selected one so positioned, bringing the stent and sleeve into an engagement; and
while maintaining the engagement, binding the stent and the sleeve together to form a composite stent graft.

18. The process of claim 17 wherein:
said selected one is the sleeve and said other is the stent, whereby said positioning comprises disposing the sleeve within the stent for said engagement and binding.

19. The process of claim 18 wherein:
said forming of a coupling comprises forming a first line of stitching running at least approximately axially of the sleeve and extending through the selected portions of the sleeve.

20. The process of claim 19 wherein:
said forming the coupling further includes forming a second line of stitching adjacent the first line of stitching, and severing the sleeve between the first and second stitching lines.

21. The process of claim 17 wherein:
said forming a coupling consists essentially of forming a single axially-extending coupling to form two of said side-by-side fluid conduits.

22. The process of claim 21 wherein:
said selected portions of the sleeve are spaced apart about 180 degrees, whereby the two side-by-side fluid conduits are approximately equal in size.

23. The process of claim 17 wherein:
said positioning of a selected one of the stent and sleeve further includes adjusting the selected one to reduce its radius from that in its nominal state, inserting the selected one into the other with the radius of the selected one reduced while maintaining the other in its nominal state, then radially expanding the selected one toward said engagement.

24. The process of claim 23 further including:
before said engagement of the stent and sleeve, applying an adhesive to at least one of the stent and sleeve.

25. The process of claim 24 wherein:
said adhesive is curable and applied uncured to the at least one of the stent and sleeve, and said binding of the stent and the sleeve comprises curing the adhesive with the stent and sleeve in said engagement.

26. The process of claim 17 wherein:
said providing a tubular stent comprises winding a plurality of structural strands into first and second sets of helices in opposite directions, and said providing a tubular sleeve comprises interweaving a plurality of compliant, substantially inextensable textile strands into third and fourth sets of helices wound in opposite directions.

27. The process of claim 26 wherein:
said winding comprises winding the structural strands so that the first and second sets of helices form a first braid angle, and interweaving the textile strands so that the third and fourth sets of helices form a second braid angle within about five degrees of the first braid angle when the stent and sleeve are in their respective nominal states.

28. A body insertable prosthesis, including:
a compliant and substantially fluid impervious sleeve having tubular proximal and distal end regions defining respective proximal end and distal end fluid conduits;
a tubular open-frame structural member surrounding the sleeve and fixed to the sleeve at least along said tubular end regions whereby the structural member and the sleeve are adjustable in concert between a nominal state and a reduced-radius state; and a flow dividing feature defining a plurality of medial fluid flow conduits along a medial region of the sleeve, wherein each of the medial conduits is open to the proximal end conduit and to the distal end conduit.

29. The prosthesis of claim 28 wherein:

the sleeve is formed of a continuous fabric wall, and the flow dividing feature comprises a coupling of selected portions of the fabric wall circumferentially spaced apart from one another when the sleeve is in a cylindrical shape.

30. The prosthesis of claim 29 wherein:

the coupling comprises a line of stitching running axially of the sleeve.

31. The prosthesis of claim 30 wherein:

the selected portions of the fabric wall are circumferentially spaced apart about 180 degrees when the sleeve is a cylinder, whereby the coupling forms two medial conduits of approximately equal size.

32. The prosthesis of claim 29 wherein:

the structural member and sleeve are reduced radially as they are elongated axially, and behave according to substantially the same relationship of radial reduction vs. axial elongation.

33. The prosthesis of claim 32 wherein:

the structural member is formed of structural strands wound in first and second sets of helices in opposite directions to form a first braid angle, and the sleeve is formed of substantially inextensable textile strands wound in third and fourth sets of helices in opposite directions to form a second braid angle within about five degrees of the first braid angle.

34. A body implantable system of prosthetic devices including the prosthesis of claim 28 and further including:

a plurality of tubular stent grafts, each tubular stent graft being adjustable between a nominal state and a radially-reduced state, each tubular stent graft further being insertable via the distal end conduit into a corresponding one of the medial conduits, and when so inserted, radially expandable into engagement with the sleeve to secure the tubular stent graft within its associated medial conduit.

* * * * *